United States Patent [19]

Meeker et al.

[11] Patent Number: 6,051,687
[45] Date of Patent: Apr. 18, 2000

[54] PURIFICATION OF LIQUID PROTEIN HYDROLYSATE AND THE RESULTANT PRODUCTS

[75] Inventors: Doyle Ervin Meeker, Onawa; Eric James Lohry, Sioux City, both of Iowa

[73] Assignee: Nutra-Flo Company, Sioux City, Iowa

[21] Appl. No.: 09/255,508

[22] Filed: Feb. 22, 1999

[51] Int. Cl.[7] .................................. C07K 1/12; C07K 1/30
[52] U.S. Cl. .................... 530/343; 530/344; 530/407; 530/420; 530/427
[58] Field of Search .................. 554/179; 71/15; 210/749, 753, 902; 426/56, 601, 608, 657, 807; 514/2.21; 435/68.1; 530/343, 344, 407, 419, 420, 427

[56] References Cited

U.S. PATENT DOCUMENTS

| | | | |
|---|---|---|---|
| 1,794,370 | 3/1931 | Frey | 426/23 |
| 2,593,487 | 4/1952 | Royal | 562/516 |
| 3,969,540 | 7/1976 | Jensen | 426/657 |
| 4,117,175 | 9/1978 | Senior | 426/657 |
| 4,130,555 | 12/1978 | Ohtsuka et al. | 426/564 |
| 4,293,571 | 10/1981 | Olofsson et al. | 426/7 |
| 4,294,856 | 10/1981 | Kinumaki et al. | 426/7 |
| 4,361,587 | 11/1982 | Brwe et al. | 426/42 |
| 4,389,423 | 6/1983 | Madsen | 426/417 |
| 4,443,540 | 4/1984 | Chervan et al. | 435/69 |
| 4,572,839 | 2/1986 | Guitteny et al. | 426/646 |
| 4,627,983 | 12/1986 | Scharf et al. | 426/7 |
| 4,847,096 | 7/1989 | Mellqvist et al. | 426/41 |
| 5,053,234 | 10/1991 | Anderson et al. | 426/59 |
| 5,290,685 | 3/1994 | Koide et al. | 435/68.1 |
| 5,356,637 | 10/1994 | Loosen et al. | 426/7 |
| 5,607,840 | 3/1997 | Van Gorp et al. | 435/68.1 |
| 5,744,179 | 4/1998 | Shimamura et al. | 426/41 |

OTHER PUBLICATIONS

Zinpro Corporation Technical Bulletin, Availa–4 Unidentified Information for Livestock Nutritional Feed(1996).

Zinpro Corp. Technical Bulletin, Zinc Methiomine(not dated) Albion Maac C–2–MZ (1995).

*Primary Examiner*—Jeffrey E. Russel
*Attorney, Agent, or Firm*—Zarley, McKee, Thomte, Voorhees & Sease

[57] ABSTRACT

A method for removing excess salts, sulfites, sulfates and fatty components from liquid protein hydrolysate is described. Purified liquid protein products having reduced concentrations of salts, sulfites, sulfates and fatty material are also described. The purified liquid protein hydrolysate product can be characterized as having lower than about 0.5% sulfites or sulfates and can also be enhanced with nutrients such as phosphate, potassium, manganese, copper, calcium, magnesium, iron, cobalt, zinc or amino acid such as methionine or lysine.

22 Claims, No Drawings

PURIFICATION OF LIQUID PROTEIN HYDROLYSATE AND THE RESULTANT PRODUCTS

BACKGROUND OF THE INVENTION

This invention relates to a method of significantly reducing the levels of sulfites, sulfates, salts and fatty components in liquid protein hydrolysate. This invention further relates to the resulting purified protein product and fatty components.

Protein hydrolysate consists of a mixture which includes amino acids and short chain peptides resulting from the hydrolysis of various animal and vegetable proteins. These protein hydrolysates may also be obtained from bacterial or yeast cultures. See for example, Scharf et al., U.S. Pat. No. 4,627,983. Protein hydrolysates are also common by-products of other procedures such as the extraction of the blood anti-coagulate heparin from porcine hash gut or intestinal mucosa.

Purified protein products from protein hydrolysate have a multitude of potential uses such as cosmetic additives, nutritional ingredients for foods and beverages, foaming agents, additives to medicinal compounds to block bitterness, sources of amino acids, additives or replacements for infant formula, and use in artificial nutrition administered orally, internally, parenterally or intravenously.

Of particular interest in the present application is the use of protein purified from protein hydrolysates as a feed ingredient for livestock starter rations. For example, University feeding trials have shown that protein hydrolysates when evaporated to a slurry of 45% solids, prove to be an excellent source of protein for pig starter rations. This reduction of water content to 55% also has shown an added benefit of reduced or eliminated problems with spoilage. Preferably the protein hydrolysates are evaporated or reduced to a 5% or less water content for efficiency and economic purposes. Nutritional uses of the purified protein hydrolysate also include such specialty feeds as milk replacers for calf, piglet and other weaning mammals, protein extender for animal feed, an amino acid supplement, and flavor or protein enhancer for human food and pet food. However, without further purification, evaporation of water from the protein hydrolysate renders a final product with higher salt and sulfite concentrations making the end product unsatisfactory for many of these uses. Further purification becomes even more important when the protein hydrolysate is reduced to a dried product thus increasing the salt and sulfite concentrations even more.

For both economic and environmental reasons, productive use is now being made of an increasing percentage of the waste material generated as a result of the slaughter of animals, such as livestock. As mentioned above, a major use of livestock waste or other by-products is in the production of the blood anti-coagulant heparin. It has been estimated that over 90% of the heparin currently used as a blood anti-coagulant is obtained from porcine intestinal mucosa. (See U.S. Pat. No. 5,607,840.) An aqueous solution containing the mucosa from the livestock waste or by-products is chemically (either by acid or alkaline treatment) or enzymatically (by protease for example) hydrolyzed. The heparin is then extracted from the hydrolyzed mucosa by techniques known to those of skill in the art, such as selective sorption using an ionic exchange resin.

The solution containing the digested tissues includes high concentrations of salt to discourage or prevent constituents other than certain anionic or polyanionic materials such as the heparin, from sticking to the resin during the sorption of these materials. In addition, the mucosa and the digest solution also contain, as a rule, an additional salt component. This additional salt component is introduced into the solution in the form of an oxygen scavenger, bacteriostat or bacteriocide, typically sodium bisulfite, which is added to stabilize the raw material and to prevent bacterial growth.

It is known that, following column purification, the high residual concentration of salt in the digestion solution renders the unabsorbed portion of the digest largely useless for most practical purposes. The salt and sulfite levels make this protein sidestream less acceptable. While sulfites can serve as an effective source of sulfur in fertilizers, prolonged usage of this concentrated protein sidestream may become potentially toxic when repeatedly applied to soil. The sidestream may also be toxic to those animals or humans allergic to sulfites.

One method of reducing the salt level is to perform enzyme hydrolysis as an alternative to chemical treatment. For example, Van Gorp et al., U.S. Pat. No. 5,607,840 teach a method of preparing protein hydrolysates from livestock by-products such as pork intestines, with an enzyme selected from the proteolytic enzymes of the Subtilisin family. Van Gorp et al. teach the use of proteolytic enzyme at salt concentrations of less than 0.1 molar, however, the need for a bacterial growth inhibitor is still recognized. Further, even in the presence of such a bacterial growth inhibitor such as 0.5% (w/v) sodium metabisulfite, if the raw material is to be transported or stored, the raw material still needs to be maintained at an elevated temperature of between 55° C. and 90° C. to avoid rapid spoilage.

While other methods have been developed that will yield purified protein products from protein hydrolysates, these methods assume that the production of the protein hydrolysate is the ultimate goal, therefore the protein source is not stored or transported for a long period of time and the creation of the protein hydrolysate will immediately precede the purification process. See Kazumasa Ohtsuka et al., U.S. Pat. No. 4,130,555; Brule et al., U.S. Pat. No. 4,361,587; and Kinumaki et al., U.S. Pat. No. 4,294,856. The use of bacterial growth inhibitors such as bacteriostats or bacteriocides are not necessary when there is no storage, transport or other conditions leading to spoilage at issue.

One method of overcoming spoilage in transport after extraction of heparin is to evaporate the water in the protein hydrolysate to a water content of 55% or less. This has the additional advantage of reducing water content in the resulting protein hydrolysate thus reducing shipping costs and further lowering costs by lowering storage volumes needed for the same amount of protein. However, by reducing water content from approximately 82% (as is found in many commercially available protein hydrolysate available as by-products from the production of heparin) to 55% or less water content the sodium sulfite levels are also being concentrated. For example, a typical level of sulfite in an 18% solid by weight liquid protein hydrolysate is 2.5% to 3.5%. However, when this same 18% solid by weight protein hydrolysate is concentrated through evaporation of the water to a water content of 55% the sulfite concentration is increased to 6.25% to 8.75% in the concentrated product. This level of sulfite is found to be undesirable by many end product users and completely unacceptable by many more. For example, the protein hydrolysates as potential sources of nutrient become unpalatable with the presence of high sulfite levels when used in the pet food market. Further, the Association of American Feed Control Officials (AAFCO) (official publication at pages 196–197) restricts the use of sulfites in meats and vitamin BI sources.

SUMMARY OF THE INVENTION

Therefore, a primary objective of the present invention is to provide a method for the reduction of sulfite concentrations in liquid protein hydrolysate. In addition, another objective is to provide a method for the reduction of the salt content of a protein hydrolysate.

A further objective of this invention is to provide a method of removal of the fatty particles in the liquid protein hydrolysate. In addition, another objective is to produce a purified fatty component product.

Yet another objective of this invention is to provide a purified protein product with a greatly reduced sulfite, sulfate and salt content.

A further objective of this invention is a method whereby selected nutrients are added to the purified protein product.

A further objective of this invention is to provide a stable form of the liquid protein hydrolysate which will have a lower tendency of spoilage.

Another objective of this invention is to provide a purified protein product that can be evaporated, even to a powder form of less than or equal to 5% water content, and that also has greatly reduced salt, sulfite, sulfate and fatty component content.

DETAILED DESCRIPTION

Protein hydrolysate has been produced as a by-product from the extraction of heparin from porcine hash gut or intestinal mucosa. This liquid protein hydrolysate by-product contains approximately 18% solids by weight and may be purchased as a secondary product from the extraction of heparin from heparin producers. Much of this by-product material has been applied to land as a fertilizer for the nitrogen value. However, due to the high salt and sulfite content of this by-product, prolonged use as a fertilizer may not be possible or economical. Also, if the material is not kept hot, greater than 140° F., the material will spoil rapidly even though sodium bisulfite has been added to the animal tissue at the packing plant as a preservative.

There are many uses for a purified protein product that can be obtained from protein hydrolysate if bisulfite has not been added. There are methods known to those of skill in the art whereby hydrolysate prepared in the absence of salt from sodium bisulfites can be purified by centrifugation, filtration, or ultra-filtration to render a final purified protein hydrolysate. See Loosen et al., U.S. Pat. No. 5,356,637, and Olofsson et al., U.S. Pat. No. 4,293,571.

In the preparation of heparin, additional salt is also required in certain methods. For example, in the method described in British Patent No. 992,201, an alkali, alkali earth metal, or ammonium salt is used as a catalyst in the reaction necessary to remove the heparin from the protein. In this method, at least 0.01 mole of a dissolved salt must be present, whereby the recommended salt is sodium chloride. The salt range in this method is recommended to fall between 0.1 and 1.0 molar.

Another commercial process presently in use for the production of heparin is based on the purification procedure described in British patent 889,648. The protein sidestream of this process also contains a high percentage of salt and sufficient water soluble quaternary ammonium salt to selectively precipitate substantially all the heparin.

In an effort to overcome high salts necessary to remove heparin with the ultimate goal of removing the high residual salt content from the protein hydrolysate, the methods for digestion of animal tissue, including animal tissue having endothelial components, have been developed utilizing enzymatic methods of digestion. See for example Van Gorp et al., U.S. Pat. No. 5,607,840. The method of Van Gorp et al. teach a protein hydrolysate may be produced by treating digested mucosa tissue with less than 0.5 molar salt, and preferably less than 0.1 molar salt being an alkali metal salt, an alkali earth metal salt, an ammonium salt of an acid, or a mixture thereof. Finally, Van Gorp et al. also teach that the digested animal solution is depleted of impurities, including heparin and certain other anionic and polyanionic impurities, by selective sorption onto an anion exchange resin. However, even with this low level of salt, there still remains the need for a bacteriostat or bacteriocide such as sodium metabisulfite to be added to the raw material for transportation and storage prior to processing. Also, if these products are evaporated to reduce water content or to remove the water, the salt concentrations increase and the sulfite and sulfate concentrations increase.

Despite an increased interest in alternate uses for the protein hydrolysate by-product of heparin extraction from animal tissue, it has not been previously known how to reduce the salt concentrations in the protein hydrolysate. The present invention provides a method for purifying the protein hydrolysate when the hydrolysate is concentrated, it results in a protein product with significantly reduced salt concentration. In addition, it has not been known how to remove the sulfites or sulfates from this protein hydrolysate so that the hydrolysate, when concentrated, results in a significantly reduced sulfite and sulfate concentrations.

Applicants have taken commercially available liquid protein hydrolysate by-product from the extraction of heparin from porcine hash gut or intestinal mucosa and have concentrated the material by evaporation of water to a slurry containing 45% of solids. As previously discussed, by reducing the water content, the problems of spoilage were overcome. However, the typical levels of sulfite of 2.5% to 3.5% in the 18% solids original protein hydrolysate were increased to 6.25% to 8.75% sulfite in the concentrated product. This level of sulfite was found to be undesirable by some customers and unacceptable by a number of others. Therefore, in one embodiment of the invention, the sulfite levels in the protein hydrolysate product is reduced to broaden the available uses of the resulting purified protein product when concentrated, including increased potential use in the starter ration or weaning programs of livestock facilities.

Initially, removal of sulfite and sulfate was attempted utilizing membrane filtration. Two materials were used in this test. One material was the normal 18% solids as received from the heparin extraction source and the other was a low fat material produced by lowering the pH of the 18% material with sulfuric acid to approximately pH 5 or less and heating the samples to about 60° C. (140° F.). This lowering of pH allowed the fatty components to float to the top and ultimately enabled the drawing of the low fat material from the bottom for the test. This removal of fat material was done as there was a concern that the fatty components would interfere with the membrane filtration. However, little difference was noted between the two materials in this study. This pilot study showed that the concept could work as the removal of sodium, chloride, and sulfur were in the range expected, however, about 10% of the crude protein separates out with the fat and the ash and sulfur content following dehydration is higher in the low fat sample. This loss of protein may be overcome through the use of different types of membranes. If the contained salts are of smaller ion size as is the case where the sulfite and sulfate have been precipitated by the addition of calcium compounds such as calcium oxide, calcium hydroxide or calcium chloride the separation may be even more selective.

In another embodiment, the method of sulfite/sulfate removal from the 18% solid protein hydrolysate is precipitation of sulfite and sulfate by adding calcium ions and removing the precipitated calcium sulfite. Applicants unexpectedly found that the fatty components interfere with the separation processes. Applicants discovered that filtration rate is substantially improved if most of the fatty components are removed prior to the addition of the calcium ion.

Fatty components can be removed by a number of methods including separation by centrifuging, decanting, or filtering. The pH of the material can be lowered whereby the fatty components tend to flocculate and rapidly float to the top. The optimum pH level for separation varies according to the method used. When separating by centrifuging or decanting, the optimum pH is around pH 6.6 as evidenced in Table 1.

TABLE 1

| pH | fatty component layer* | clear protein hydrolysate* |
| --- | --- | --- |
| ≧7.2 | little separation observed | |
| 7.0 | 50% | 50% |
| 6.8 | 30% | 70% |
| 6.6 | 25% | 75% |
| 6.4 | 33% | 67% |
| <6.4 | 45% | 55% |

*percentages given are Volume/Volume

Separation by filtration is better at lower pH levels. For example, at pH 7.0 the filter paper blinds immediately and at pH 6.0 there is some improvement, although the filter still blinds. At pH 5.0 and below the filtration is rapid and the filter paper does not blind.

Separation is also temperature dependent as evidenced by an improved separation when the material is heated above room temperature. The separations in Table 1 were conducted on material that had been heated to about 125° F. (52° C.). The filtration tests were conducted on material that had been heated to 170–190° F. (76.7–87.8° C.).

In another embodiment, filtration through a rotary precoat filter to remove the fatty components results in a protein hydrolysate more conducive to precipitation of sulfites. However, in this method a filter aid such as diatomaceous earth, perlite or cellulose is used. A portion of this filter aid is usually discharged with the fatty components and insoluble materials rendering the fatty product less suitable as a marketable by-product.

In another embodiment, the use of hydrochloric acid to lower the pH results in a higher chloride concentration in the protein hydrolysate. If calcium chloride is used to precipitate calcium sulfite, sodium chloride is the primary salt left in solution. The calcium sulfite can be removed by filtration, centrifugation, or decanting. After the removal of the sulfite compounds the remaining material can be passed through a membrane filter to remove sodium and chloride.

In yet another embodiment, other calcium compounds such as calcium hydroxide or calcium oxide can be used to precipitate the sulfite. In all of these embodiments, the calcium sulfite can be removed by filtration, centrifugation, or decanting. If calcium compounds such as calcium hydroxide or calcium oxide are used to precipitate the sulfite, no chloride is added to the system. However, in this case, the pH of the final material would be higher, typically in the range of pH 9 to 12. This pH may be lowered by the addition of an acid. Alternately, the high pH material may be filtered through a membrane filter to remove sodium, hydroxide, and chloride. Removal of hydroxide ions would lower the pH of the material and not require the addition of an acid to adjust the pH to more desirable levels.

In another embodiment, protein hydrolysate is purified by first lowering the pH by addition of acid and separation of the fatty components by centrifuging, filtering and decanting. Calcium chloride is then added to precipitate the sulfite and the calcium sulfite is then removed by filtration centrifugation or decanting. Sodium hydroxide can be added to produce a product with a neutral pH if desired. In an alternative embodiment, potassium hydroxide can be added to produce a product with a neutral pH and has the added advantage of adding potassium ions to the purified protein product. After removal of the sulfite compound the material can then be passed through a membrane filter to remove the sodium and chloride resulting in a low ash product with high protein content.

In yet another preferred embodiment, the fatty components are removed as described above, but calcium hydroxide or calcium oxide are used to precipitate the sulfite. This adds less chloride to the system. The calcium sulfite again can be removed by filtration, centrifugation or decanting, however the pH of the final material is in the range of pH 9–12 and is lowered by the addition of phosphoric acid resulting in a final product containing phosphorus as a desirable nutrient. This results in a protein hydrolysate with a somewhat lower protein content and somewhat higher ash content than in the membrane filtration method.

In another embodiment sulfuric acid is used to lower the pH, both sulfite and sulfate precipitate as insoluble calcium compounds and can be removed by filtration, centrifugation or decanting. Use of calcium chloride leaves residual chloride which would be present as sodium chloride. Other than increasing the ash content, the presence of salt may not be detrimental. If calcium hydroxide or calcium oxide is used to precipitate the sulfite and sulfate the pH of the material will be in the range of 9 to 12. Addition of phosphoric acid to lower the pH may be used with the additional advantage of adding phosphorus as a desirable nutrient.

In yet another embodiment, the fatty components removed from the protein hydrolysate can be used as a food or industrial component for many products, including reinsertion in the final purified protein product of the present invention.

The following examples involve experiments conducted which demonstrate how the above-stated embodiments were reached. They are not meant to limit the present invention in any manner. All references to patents, journal articles or other publications cited previously or hereinafter are hereby expressly incorporated in their entirety by reference.

Further it is understood that trivial modifications would be known to those of skill in the art and are also understood to be included within the scope of the present invention as described and claimed herein.

EXAMPLES

Example 1

A 100 gram sample of low fat protein hydrolysate containing 18% solids, 1.6% $SO_3$ at a pH of 4.8 was heated to 160° F. and treated with calcium hydroxide. The material was then filtered and the $SO_3$ measured at 0.1%. The pH was adjusted to pH 7 with a phosphoric acid and a slight precipitate occurred.

Example 2

A sample of 18% solids protein hydrolysate was split into two parts. One part was analyzed without further treatment (Hi-Fat) and the other part was treated with sulfuric acid to lower the pH to 5 and the fat was separated (Lo-Fat). The $SO_3$ in the Lo-Fat portion was measured at 32,400 ppm. A 1000 g portion was heated to 170° F. and 60 grams calcium hydroxide was added and the mixture stirred for two hours. The mixture was then filtered to remove the solids and the $SO_3$ level was measured at 560 ppm.

Example 3

A 3000 grams sample of 18% protein hydrolysate was treated with 120 grams of 22°Be' hydrochloric acid to lower the pH to 5. After separating the fatty components, a 1000 gram portion heated to 170° F. was treated with 35 grams of calcium hydroxide, stirred for two hours and filtered to remove the precipitated solids. The remaining $SO_3$ was measured at 395 ppm and $SO_4$ at 182 ppm.

Example 4

A 200 gram sample of 18% protein hydrolysate, pH 7.725 was treated with 3.741 grams of 96.3% sulfuric acid to lower the pH to 5 for separation of the fatty components. The mixture was heated to 170° F. and filtered through Whatman GF/A. The recovered filter cake weighed 22.9 grams and the filtrate weighed 154.9. Some loss could be accounted for by evaporation of water during the heating to 170° F. The $SO_3$ content of the filtrate was measured at 29,400 ppm $SO_3$. A 2× stoichiometric amount of calcium hydroxide based on the $SO_3$ analysis and the calculated amount of $SO_4$ added to lower the pH was calculated to be 13.78 grams. The mixture was kept hot and stirred for 2 hours. The solids were then filtered out and yielded 38.8 grams of wet filter cake and 137.2 grams of filtrate. The pH of the filtrate was 12.1 and the $SO_3$ was 310 ppm. The high pH is due to the excessive addition of calcium hydroxide.

Example 5

Protein hydrolysate made from hand-stripped mucosa is lower in fatty components. It was considered possible with the lower fatty composition that the fatty component separation step could be eliminated. A 100 gram sample of such material containing 31,800 ppm $SO_3$ was treated with 3 grams of calcium hydroxide. The mixture was heated to 170° and stirred for 30 minutes. The material was then poured into a Buchner funnel under a vacuum of 26 inches of Hg with a Whatman 41 filter paper in place. Only a few drops of liquid passed through the filter before the surface blinded completely.

Example 6

A 3000 grams sample of 18% solids protein hydrolysate was treated with 59.16 grams of 66° Be' technical grade sulfuric acid to lower the pH to 5. The mixture was then heated to 170° F. and used as a feed material in a Door-Oliver filter leaf test apparatus to estimate approximate filtration rates for removal of fatty components through a rotary precoat vacuum filter. After compacting the filter aid with several initial filtrations the typical flow rate achieved ranged from 10.5 to 13.5 gallons per hour per square foot (gph/sqft). The specific gravity of the filtrate was 1.088 or 9.06 lb/gal. Flow rates to be expected should range from about 95 to 122 lbs/hr/sqft. A rate of 10 tons per hour (tph) would require a 200 sq ft filter.

Example 7

The filtrate from experiment 6 was analyzed at 31,100 ppm $SO_3$. A calculated stoichiometric amount of calcium hydroxide needed to precipitate the $SO_3$ and the $SO_4$ added from sulfuric acid was 4.3 grams/10 grams filtrate. A 500 grams portion of the filtrate was heated to 160° F. and 21.5 grams of calcium hydroxide was added with stirring. At intervals portions of the mixture was removed, filtered and the filtrate checked for $SO_3$. It appears that the reaction is essentially over in less than 15 minutes. The tabulated results are:

| Time (mins) | ppm $SO_3$ | pH | Temp (deg. F.) | Comments |
|---|---|---|---|---|
| 15 | 5486 | 9.535 | 180 | Filters well |
| 30 | 5649 | 9.407 | 150 | Filters OK |
| 45 | 5472 | 9.503 | 120 | Filters slow |
| 60 | 5192 | 9.419 | 180 | Filters OK (sample was heated) |
| 2 days | 3450 | 9.419 | 120 | Filters slower |

Example 8

A second 500 gram portion of the material from experiment 6 was heated to 150° F. and treated with 26.14 grams of calcium hydroxide or approximately 122% of the calculated stoichiometric amount. The procedure of experiment 7 was repeated with the exception that the time intervals for sampling were shortened. It appears that most of the reaction is completed within about 6 minutes. The tabulated results are:

| Times (mins) | ppm $SO_3$ |
|---|---|
| 1 | 3648 |
| 3 | 2272 |
| 6 | 1721 |
| 10 | 1574 |
| 15 | 1438 |
| 30 | 1378 |

Example 9

A sample of protein hydrolysate containing approximately 18% solids was passed through a membrane filtration apparatus. A comparison of the chemical analysis of the feed material with the resultant product showed a decrease in:

1. Ash content by 25%;
2. Chloride content by 60%;
3. Sodium content by 25%; and
4. Potassium content by 25%.

This reduction in sodium, potassium and chloride content indicates that membrane filtration would be effective in separating these smaller ions from the higher molecular weight proteins.

We claim:

1. A method for removal of sulfite and sulfate from a liquid protein hydrolysate comprising:
   adding calcium ions to precipitate the sulfite and sulfate; and
   removing the precipitated sulfite and sulfate.

2. The method of claim 1 wherein the method further comprises the step of removing fatty components from the liquid protein hydrolysate prior to adding the calcium ions wherein the fatty components are removed by adding an acid until pH is lowered for separation of fatty components and liquid protein hydrolysate and removing the fatty components by centrifuging, filtering or decanting.

3. The method of claim 2 wherein the acid is selected from the group consisting of:

hydrochloric acid, phosphoric acid, sulfuric acid, and citric acid.

4. The method of claim 1 where the source of the calcium ion is calcium chloride.

5. The method of claim 1 wherein the method further comprises a filtration step of, after removing the sulfite and sulfate, filtering the protein hydrolysate through a membrane filter whereby remaining sodium, chloride, and hydroxide are removed.

6. The method of claim 2 wherein the method further comprises raising the pH to about neutral using a hydroxide or an oxide after removing the fatty components.

7. The method of claim 6 wherein the hydroxide is selected from the group consisting of: sodium hydroxide, potassium hydroxide, calcium hydroxide and an alkali hydroxide.

8. The method of claim 1 wherein the source of calcium ions are selected from the group consisting of: calcium chloride, calcium hydroxide, and calcium oxide.

9. The method of claim 1 wherein the source of the calcium ions is calcium hydroxide or calcium oxide.

10. The method of claim 9 wherein the method further comprises a final step of lowering the pH of the protein hydrolysate to about neutral using an acid.

11. The method of claim 10 wherein the acid is selected from the group consisting of: phosphoric acid, citric acid, hydrochloric acid, and sulfuric acid.

12. A method for producing a purified protein product from liquid protein hydrolysate having fatty components, sulfites, and sulfates, comprising:

adding an amount of acid to a liquid protein hydorlysate sufficient to lower the pH for separation of fatty components and liquid protein hydrolysate;

heating to about 125°–190° F.;

removing the fatty components;

adding calcium ions sufficient to precipitate the sulfite and sulfate; and removing precipitated sulfite and sulfate by filtrating, centrifuging or decanting to produce a purified protein product.

13. The method of claim 12 wherein the acid is selected from the group consisting of: hydrochloric acid, sulfuric acid, phosphoric acid, and citric acid.

14. The method of claim 12 wherein the source of the calcium ions is calcium hydroxide or calcium oxide.

15. The method of claim 14 further comprising a final step of adding sufficient acid to bring pH to about neutral.

16. The method of claim 15 wherein the acid is selected from the group consisting of: hydrochloric acid, sulfuric acid, phosphoric acid, and citric acid.

17. The method of claim 14 further comprising final steps of:

removing sodium, chloride, and hydroxide by filtering through a membrane; and adding sufficient phosphoric acid to bring pH to about neutral.

18. The method of claim 12 wherein the source of the calcium ions are calcium chloride.

19. The method of claim 18 further comprising final steps of:

adding sufficient sodium hydroxide or potassium hydroxide to bring pH to about neutral; and removing sodium, chloride, and hydroxide by filtering through a membrane.

20. The method of claim 12 wherein the fatty component is removed by centrifuging, filtering, or decanting.

21. The method of claim 12 wherein the fatty component is removed by filtering through a filter.

22. The method of claim 1 wherein the final sulfite or sulfate concentration is less than about 0.5% by volume.

* * * * *